United States Patent [19]

Renga

[11] Patent Number: 4,658,041

[45] Date of Patent: Apr. 14, 1987

[54] PREPARATION OF ALKYL CARBONATES

[75] Inventor: James M. Renga, Midland, Mich.

[73] Assignee: The Dow Chemical Company, Midland, Mich.

[21] Appl. No.: 422,762

[22] Filed: Sep. 24, 1982

[51] Int. Cl.[4] .................... C07D 317/36; C07C 68/06
[52] U.S. Cl. .................................... 549/229; 549/230; 558/260
[58] Field of Search ................. 549/229, 230; 260/463

[56] References Cited

FOREIGN PATENT DOCUMENTS 7244  1/1980  Japan .

OTHER PUBLICATIONS

Chemical Abstracts (1980) 93: 71027v.
Chemical Abstracts (1982) 96: 217206p.
D. Bencivengo et al, J. Org. Chem. (1981) vol. 46(25) pp. 5222-52224.
A. Arbin et al, J. Chromatography (1980) vol. 196, pp. 255-263.
D. Grobelny et al, Tetrahedron Letters No. 28 (1979) pp. 2639-2642.
Carl R. Noller, Chemistry of Organic Compounds (1965) pp. 332-333.

*Primary Examiner*—Norma S. Milestone
*Attorney, Agent, or Firm*—N. L. Sims

[57] ABSTRACT

Carbonate compounds are prepared by equilibrium interchange of carbonate functionality between lower alkyl carbonates especially dimethyl carbonate and alkyl halides such as allyl chloride at about 50° C. to about 250° C. in the presence of an initiator such as homogeneous or heterogeneous amines, phosphines, and ammonium or phosphonium quaternary salts.

3 Claims, No Drawings

PREPARATION OF ALKYL CARBONATES

BACKGROUND OF THE INVENTION

The present invention relates to a process for forming alkyl carbonates. In particular, the present invention relates to the preparation of alkyl carbonates by the equilibration exchange of alkyl moieties between an alkyl carbonate and an alkyl halide.

In U.S. Pat. No. 3,803,201 the preparation of dimethyl carbonate by methanolysis of alkylene carbonates is disclosed. Accordingly, a substantial excess of methanol was reacted with an alkylene carbonate in the presence of a basic catalyst.

It is known that alkyl halides may be converted to alkyl carbonates by reaction with certain inorganic salts. Disadvantageously, however, the known process also produces stoichiometric amounts of halide salt by-products. The processes are typically conducted in polar aprotic solvents such as dimethylformamide or dimethylsulfoxide.

SUMMARY OF THE INVENTION

According to the present invention, carbonate compounds corresponding to the formula $R\,OC(O)OR_1'$ or $$R_2OC(O)O$$

are prepared by contacting a lower alkyl carbonate or halogenated lower alkyl carbonate corresponding to the formula $ROC(O)OR$ with a primary alkyl halide corresponding to the formula $R_1X$ or a vicinal alkyl dihalide having one primary halide functionality corresponding to the formula $X-R_2-X$ at about 50° C.–250° C. in the presence of an effective amount of an initiator. In the above formulas, R is independently each occurrence lower alkyl or halogenated lower alkyl;

$R_1$ different than R and is an alkyl radical of up to about 20 carbons optionally further substituted with an alkenyl, aryl, halo, alkoxy, or a cyclic aliphatic or aromatic group;

$R_1'$ is R or $R_1$;

$R_2$ is $$-CH_2-CH-R'$$

where R' is R or phenyl; and

X is a halo group, preferably chloro.

In the preferred process one reactant is dimethyl carbonate which reacts in equal molar proportions with a primary alkyl chloride, $R_1Cl$, to form alkyl methyl carbonates of the formula $R_1OC(O)OCH_3$. A particularly preferred product is allyl methyl carbonate, $CH_2=CHCH_2OC(O)OCH_3$, formed by the reaction under the above reaction conditions between allyl chloride and dimethyl carbonate.

Allyl methyl carbonate as well as other carbonates prepared by the present invention is a useful intermediate that may be converted to monomers for preparation of allylic resins. In addition, the invented process allows for the preparation of alcohols from alkyl halides. For example, allyl chloride may be first converted to allyl methyl carbonate by the above process which upon methanolysis substantially according to the conditions taught in previously mentioned USP 3,803,201, yields allyl alcohol, a compound having significantly greater commercial value than allyl chloride. Similarly, propylene dichloride and bis(1-chloro-2-propyl)ether, normally considered to be by-products of little value may be converted to propylene glycol and dipropylene glycol by the invented process.

DETAILED DESCRIPTION OF THE INVENTION

In the reaction of the di(lower)alkyl carbonate or halogenated di(lower)alkyl carbonate and the primary alkyl halide or dihalide described above, a by-product recovered from the reaction is a lower alkyl halide, such as methyl chloride, which normally is removed from the reaction vessel as it is formed, thus separating it from the carbonate reactants and products and driving the equilibrium interchange reaction towards completion. The reaction process is described by means of the following schematic equation:

$$RRCO_3 + R_1X \longrightarrow R_1RCO_3 + RX$$

$$RRCO_3 + X-R_2-X \longrightarrow R_2OC(O)O + 2RX.$$

For this reason, R is preferably methyl thereby providing a highly volatile and commercially valuable by-product, methyl chloride. Removal of such by-products from the reaction vessel may be assisted by use of an inert sweep gas if desired. In addition to avoid ether formation, it may be desirable to employ elevated pressures of carbon dioxide. However, adequate reaction rates and selectivities may be obtained without the use either of a sweep gas or of elevated pressures. Suitable reaction pressures are from about atmospheric to about 1000 psig.

The proportions of reactants used are not critical. However, to avoid unnecessary purification steps it is preferable to employ stoichiometric amounts of carbonate and halide reactants.

The reaction can be run effectively at any temperature within the defined range but is preferably conducted at temperatures from about 130° C.–160° C. At such temperatures the reaction time may vary from several minutes to several hours depending on the reactants involved. Under continuous process conditions, the residence time of the halide and carbonate reactants under reaction conditions will determine the amount of products formed.

The reaction is initiated by the presence of one of several suitable initiators. Basic catalysts, such as alkali metal alkoxides, salts of a strong base and a weak acid, or non-nucleophilic organic bases are suitable. The latter class consists in practice of tertiary amines or phosphines, both aliphatic and aromatic of up to about 30 carbons. Suitable basic catalysts include triethylamine, tributylamine, dimethyl benzoxyethylamine, pyridine, quinoline, triphenylphosphine, N,N-dimethylaminopyridine, etc., alkali metal carbonates, acetates and alkoxides. Additional suitable initiators include alkaline metal halides and stable quaternary salts such as ammonium or phosphonium quaternary salts having inert counterions. A preferred alkali metal halide is lithium chloride. Preferred quaternary salts have the general formula $(R'')_4AY$ where each $R''$ is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate. The $R''$ groups may be alkyl, aryl, alkaryl, aralkyl, or cycloalkyl. Also, two $R''$ groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts. The catalytic salt may be added as such to the reaction mixture or it may be formed in situ.

The quantity of initiator compound is not critical so long as any significant amount is present and available at the reaction site. Suitably from about 0.01 to 10 percent of initiator based on the weight of the reactants is used. Larger amounts of initiator may be employed but may complicate the ability to produce pure product.

The previously mentioned initiator should be at least partially soluble in the reaction mixture and it be advantageous in accomplishing this goal to employ an additional agent to render the initiator soluble in the reaction medium. Suitable agents, referred to hereinafter as "solubilizing agents", which are particularly suitable for use with basic catalysts and alkali metal halides include the compounds generally known as phasetransfer catalysts such as, for example, hexamethylphosphoramide or the cyclic oligomers of ethylene oxide known as crown ethers. Such solubilizing agents may be employed in minor amounts, for example, in the ratio of about 0.005 to 10 moles per mole of initiator.

In a mode of the invention particularly adapted to continuous operation, one or more R groups may be pendant methylene groups from a resin matrix so that the quaternary salt is a salt form of a strong base anion-exchange in such as DOWEX ® 21K, DOWEX ® 11, DOWEX ® MWA-1, or other such commercially available ion-exchange resins or the phosphonium equivalents of such quaternary ammonium-substituted resins. Also suitable are heterogeneous amine or phosphine functionalized resins such as the weak base anion-exchange resins or other polymerically-bound amine or phosphines. A particular example of a polymerically-bound phosphine is poly(diphenylphosphinestyrene) in bead form, cross-linked with divinylbenzene. Such polymerically-bound phosphines may be prepared by treatment of polystyrene with a 1:1 complex of butyllithiumtetramethylenediamine in cyclohexane followed by quenching with chlorodiphenylphosphine.

Preferred catalysts are tertiary amines or phosphines either in the homogeneous phase or heterogeneously bound to polymer supports such as polystyrene. Under the reaction conditions employed it is believed that the amine and phosphine compounds form in situ a quaternary salt by reaction with the alkyl halide reactant.

The reactor may be constructed of any suitable material considering the elevated temperatures and optionally elevated pressures employed. Due to the generation of small amounts of hydrogen chloride during the process, acid resistant materials are most suitable for use. A reactor of stainless steel, such as Hastelloy C, or a Teflon ®-lined steel reactor is preferred.

Under some reaction conditions it may be found advantageous to add a polymerization inhibitor in order to prevent polymerization of polymerizable reactants such as allyl halides and allyl methyl carbonates if such are present. Under such circumstances p-methoxyphenol or a similar compound may be employed as an effective radical polymerization inhibitor.

A solvent may be employed if desired depending on the nature of the carbonate and alkyl halide reactants. Preferred solvents are inert, high boiling, polar solvents, such as sulfolane, glycol diethers and substituted aromatic compounds such as anisole or o-dichlorobenzene. Preferred solvents are amides such as N,N-dimethylformamide or N,N-dimethylacetamide whereby the reaction is facilitated and catalyzed by small amounts of quaternary salt formed in the reaction mixture from the amide solvent. Little or no additional catalyst is needed with such a solvent which serves as both a beneficial reaction medium and a source of reaction catalyst. Additional nitrogen-containing solvents capable of forming a quaternary salt in significant quantity under the instant reaction conditions may also be employed, for example, alkylated pyridine compounds may suitably be used.

SPECIFIC EMBODIMENTS

Having described the invention, the following examples are provided as further illustrative and are not to be construed as limiting its scope.

EXAMPLE 1-15

Allyl chloride (38.3 g, 0.5 mole), dimethyl carbonate (45.0 g, 0.5 mole), p-methoxyphenol (0.25 g, 2.0 mmole) and 0.01 mole of the catalysts identified in Table I are combined in a 300-ml Paar bomb having its inside, stirrer and cooling coil coated with Teflon ®. The reactor is flushed with oxygen to help inhibit polymerization, and heated to 150° C. under 750 psig of carbon dioxide. After 2 hours, the bomb is cooled to 5° C. and vented. The contents are analyzed by capillary gas chromatography using a toluene standard. Typical results are contained in Table I.

TABLE I

| Example | Catalyst | % Conversion[a] | % Selectivity[b] |
|---|---|---|---|
| 1 | n-Bu$_4$PBr | 25.3 | 85.3 |
| 2[c] | n-Bu$_4$PBr | 35.0 | 79.6 |
| 3[d] | n-Bu$_4$PBr | 22.6 | 85.3 |
| 4[e] | n-Bu$_4$PBr | 36.0 | 83.9 |
| 5[f] | n-Bu$_4$PBr | 20.2 | 87.7 |
| 6 | n-Bu$_4$PCl | 29.7 | 76.1 |
| 7 | φ$_4$PBr | 5.3 | 95.5 |
| 8 | φ$_3$P | 1.5 | 83.3 |
| 9 | φ$_3$P/LiBr | 9.6 | 86.5 |
| 10 | φ$_3$P/LiCl[d] | 17.3 | 88.2 |
| 11 | NMP/LiCl[g] | 0.3 | 100.0 |
| 12 | 18-c-6/KCl[h] | 0.4 | 87.0 |
| 13 | imidazole | 5.7 | 83.3 |
| 14 | DMAP[i] | 25.5 | 79.5 |
| 15 | φCH$_2$N(CH$_3$)$_2$ | 16.0 | 91.2 |

[a] allyl chloride conversion based on gas chromatograph analysis of total allyl functionality recovered
[b] allyl methyl carbonate selectivity, minor component is diallyl carbonate; only trace amounts of alkyl ethers are observed
[c] 6 hours reaction time
[d] no oxygen flush
[e] 200 psi CO$_2$
[f] 140° C.
[g] NMP = N—methylpyrolidone, 6 hours of reaction time
[h] 18-crown-6-polyether, 6 hours of reaction time
[i] N,N—dimethylaminopyridine

EXAMPLES 16-19

The reaction conditions of Examples 1-14 are substantially repeated excepting that reduced pressures are employed. The amount of catalyst employed is 0.01 mole. Reaction times are 2 hours. Results are contained in Table II.

TABLE II

| Example | Catalyst | Pressure (psi) Pre-reaction | Pressure (psi) Post-reaction | Conversion[a] | Selectivity[b] |
|---|---|---|---|---|---|
| 16 | HMPA/LiCl[c] | 0 | 110 | 1.8 | 100.0 |
| 17 | n-Bu$_4$PBr | 0 | 200 | 19.0 | 88.0 |
| 18 | φCH$_2$OC$_2$H$_4$N(CH$_3$)$_2$ | 0 | 170 | 11.2 | 100.0 |
| 19 | φN(CH$_3$)$_2$ | 0 | 200 | 4.7 | 100.0 |

[a] allyl chloride conversion based on gas chromatograph analysis of total allyl functionality recovered
[b] allyl methyl carbonate selectivity, minor component is diallyl carbonate; only trace amounts of alkyl ethers are observed
[c] hexamethylphosphoramide-0.01 mole, LiCl-0.01 mole

EXAMPLES 20-30

The reaction conditions of Examples 1-14 are substantially repeated employing heterogeneous catalysts and reaction conditions further described in Table III. Reaction times are 2 hours. Results are contained in Table III.

TABLE III

| Example | Catalyst | Amount grams | Amount moles | Pressure (psi) Pre-reaction | Pressure (psi) Post-reaction | % Conversion[a] | % Selectivity[b] |
|---|---|---|---|---|---|---|---|
| 20 | ℗ -Pφ$_2$ | 10 | 0.009 | 750 | 800 | 32.0 | 87.5 |
| 21 | reuse Ex. 20 | — | — | 550 | 750 | 8.6 | 94.6 |
| 22 | reuse Ex. 21 | — | — | 550 | 750 | 2.9 | 90.0 |
| 23 | DOWEX ® MSA-1[d] | 10 | 0.04 | 550 | 750 | 6.6 | 80.0 |
| 24 | DOWEX ® MWA-1[e] | 10 | 0.04 | 550 | 750 | 55.3 | 68.3 |
| 25 | DOWEX ® MWA-1[e] | 10 | 0.04 | 0 | 220 | 34.5 | 77.6 |
| 26 | Reuse Ex. 25 | — | — | 0 | 200 | 12.8 | 84.9 |
| 27 | ℗ -PBu$_3$Br[f] | 4.97 | 0.01 | 0 | 200 | 11.7 | 87.0 |
| 28 | Reuse Ex. 27 | — | — | 0 | 160 | 9.5 | — |
| 29 | Amberlyst A-21[g] | 10 | ~0.04 | 0 | 260 | 34.9 | 77.3 |

Footnotes
[a] allyl chloride conversion based on gas chromatograph analysis of total allyl functionality recovered
[b] allyl methyl carbonate selectivity, minor component is diallyl carbonate; no alkyl ethers are observed
[c] poly(diphenylphosphinestyrene), 1.8% divinylbenzene cross-linked, 0.87 meq P/g
[d] A strong base macroporous styrene-divinylbenzene resin in the chloride ion form available commerically from The Dow Chemical Company
[e] A weak base macroporous styrene-divinylbenzene resin available commercially from The Dow Chemical Company
[f] 3-Poly(benzoxypropyltributylphosphoniumbromidestyrene)-6% divinylbenzene cross-linking, 2.03 meq P/g
[g] A strong base macroporous styrene-divinylbenzene resin in the chloride ion form available commercially from Rohm and Haas Company

EXAMPLE 30

The reaction conditions of Example 1 are substantially repeated employing allyl chloride (76.5 g, 1.0 mole), dimethyl carbonate (90.0 g, 1.0 mole), tetra-n--butylphosphonium bromide (6.78 g, 0.02 mole) and p-methoxyphenol (0.5 g, 0.004 mole) polymerization inhibitors. After heating for 7 hours at 150° C. and 600 psi carbon dioxide pressure, the reactor is cooled to room temperature and vented. Distillation gives 29.0 g (25 percent yield) of allyl methyl carbonate having b.p. of 79° C.-80° C. (150 torr) and 4.8 g (3.4 percent yield) of diallyl carbonate having b.p. of 107° C.-108° C. (150 torr).

EXAMPLE 31

The procedure employed in Example 30 is substantially repeated employing polystyrene-bound benzyl-tri-n-butylphosphonium chloride (2 percent cross-linked with divinylbenzene) as the catalyst. Accordingly, 15 g of the polymeric catalyst, allyl chloride (76.5 g, 1.0 mole), dimethyl carbonate (90.0 g, 1.0 mole) and p-methoxyphenol (0.5 g, 0.004 mole) are combined in a reactor and heated for 6 hours at 150° C. under 600 psi carbon dioxide. The reactor is then cooled to room temperature and vented. After separating the catalyst by filtration, allyl methyl carbonate (23.8 percent yield) and diallyl carbonate (2.0 percent yield) are obtained by distillation.

EXAMPLE 32

Preparation of Propylene Carbonate

The reaction conditions of Examples 1-15 are substantially repeated employing 1,2-dichloropropane (56.5 g, 0.5 mole), dimethyl carbonate (45.0 g, 0.5 mole) and polystyrene-bound benzyltri-n-butylphosphonium chloride (2 percent cross-linked with divinylbenzene, ~2 meq/g) (20.0 g). After heating for 8 hours at 150° C. and 600 psi carbon dioxide, the reactor is cooled to room temperature and vented. The catalyst is removed by filtration. Distillation gives propylene carbonate (3.0 g, 5.8 percent yield), b.p. 113° C.-114° C. (15 torr).

EXAMPLE 33

Preparation of Monocarbomethoxy Glycerol Carbonate

The reaction conditions of Examples 1-15 are substantially repeated employing 4-chloromethyl-1,3-dioxol-2-one (68.0 g, 0.5 mole), dimethyl carbonate (90.0 g, 1.0 mole) and tetra-n-butylphosphonium bromide (1.7 g, 0.005 mole). After heating for 6 hours at 150° C. and 750 psi carbon dioxide pressure, the reactor is cooled to room temperature and vented. Analysis by gas chromatography indicates a 35 percent conversion of 4-chloromethyl-1,3-dioxol-2-one. The predominate product is monocarbomethoxy glycerol carbonate,

CH$_2$OC(O)OCHCH$_2$OC(O)OCH$_3$.

The product (22.0 g, 25 percent yield based on starting 4-chloromethyl-1,3-dioxol-2-one), m.p. 86° C.-87° C., is isolated by crystallization from acetone/diethyl ether.

EXAMPLE 34

Preparation of Benzyl Methyl Carbonate

Benzyl chloride (31.65 g, 0.25 mole), dimethyl carbonate (90.0 g, 1.0 mole), tetra-n-butylphosphonium bromide (3.39 g, 0.01 mole) and N,N-dimethylformamide (200 ml) are heated to 117° C.-118° C. for 6 hours. After heating is discontinued the reaction mixture is added to 300 ml of diethyl ether and 300 ml of water. The organic layer is washed with 3×100-ml allotments of water followed by 2×100 ml-portions of 10 percent aqueous HCl, 100 ml of saturated aqueous NaHCO$_3$ and 100 ml of a saturated aqueous NaCl solution, and dried over MgSO$_4$. After solvent removal, distillation gives 27.02 g (65 percent yield based on benzyl chloride) of benzyl methyl carbonate, b.p. 110° C.-111° C. (11 torr).

EXAMPLE 35

Preparation of Methyl 1-Octyl Carbonate

1-Chlorooctane (37.17 g, 0.25 mole), dimethyl carbonate (90.0 g, 1.0 mole), tetra-n-butylphosphonium bromide (3.39 g, 0.01 mole) and N,N-dimethylformamide (200 ml) are heated to 115° C. for 24 hours. After work-up as described for Example 34, distillation gives 34.8 g (74 percent yield based on 1-chlorooctane) of methyl 1-octyl carbonate, b.p. 113° C.-114° C. (17 torr) and 1.9 g (5 percent yield based on n-octyl chloride) of di-1-octyl carbonate, b.p. 129° C.-130° C. (0.5 torr).

EXAMPLE 36

Preparation of Methyl 1-Octyl Carbonate

1-Bromooctane (48.28 g, 0.25 mole), dimethyl carbonate (90.0 g, 1.0 mole), tetra-n-butylphosphonium bromide (3.39 g, 0.01 mole) and N,N-dimethylformamide (200 ml) are heated to 115° C. for 24 hours. After work-up as described for Example 34, distillation gives 7.5 g (16 percent yield based on 1-bromooctane) of methyl 1-octyl carbonate and 4.4 g (12 percent yield based on 1-bromooctane) of di-1-octyl carbonate.

EXAMPLE 37

Preparation of Methyl 1-Octyl Carbonate

1-Chlorooctane (297.36 g, 1.0 mole), dimethyl carbonate (450 g, 5.0 moles) and 30.0 g of DOWEX® MWA-1 beads (Trademark of The Dow Chemical Company) are combined in a 2-liter stainless steel Paar bomb. The reactor is pressurized to 100 psi of carbon dioxide and heated with stirring to 150° C. After 2 hours, the bomb is cooled to room temperature and vented. After separating the catalyst by filtration, distillation gives 28.1 g (15 percent yield based on starting 1-chlorooctane) of methyl 1-octyl carbonate.

EXAMPLE 38

Preparation of 1-Buten-3-yl Methyl Carbonate and 2-Buten-1-yl Methyl Carbonate 3-Chloro-1-butene (181.1 g, 2.0 moles), dimethyl carbonate (450.0 g, 5.0 moles), tetra-n-butylphosphonium bromide (13.56 g, 0.04 mole) and p-methoxyphenol (1.6 g, 0.013 mole) are combined in a 2-liter stainless steel Paar bomb. The reactor is pressurized to 50 psi of carbon dioxide and heated with stirring to 150° C. After 3 hours, the bomb is cooled to room temperature and vented. Distillation gives 8.6 g (3.3 percent yield based on starting 3-chloro-1-butene) of 1-buten-3-yl methyl carbonate, b.p. 78° C.-80° C. (100 torr) and 49.7 g (19.1 percent yield based on starting 3-chloro-1-butene) of 2-buten-1-yl methyl carbonate, b.p. 94° C.-95° C. (100 torr).

EXAMPLE 39

Preparation of Methallyl Methyl Carbonate

The reaction conditions of Example 37 are substantially repeated employing 3-chloro-2-methyl-1-propene (181.1 g, 2.0 moles), dimethyl carbonate (450.0 g, 5.0 moles), 30.0 g of DOWEX® MWA-1 beads and p-methoxyphenol (1.0 g, 0.08 mole). After 2 hours at 150° C., distillation gives 37.7 g (15.3 percent yield based on 3-chloro-2-methyl-1-propene) of methallyl methyl carbonate, b.p. 89° C.-90° C. (100 torr) and 1.2 g (0.7 percent yield based on 3-chloro-2-methyl-1-propene) of bis(2-methylallyl)carbonate, b.p. 87° C.-88° C. (17 torr).

EXAMPLE 40

Preparation of 4-Chlorobutyl Methyl Carbonate

The reaction conditions of Example 37 are substantially repeated employing 1,4-dichlorobutane (190.52 g, 1.5 moles), dimethyl carbonate (135.0 g, 1.5 moles) and 30.0 g of DOWEX® MWA-1 beads. After 2 hours at 150° C., distillation gives 34.5 g (13.8 percent yield based on 1,4-dichlorobutane) of 4-chlorobutyl methyl carbonate, b.p. 66° C.-67° C. (0.5 torr).

What is claimed is:

1. A process for preparing carbonate compounds corresponding to the formula $R_1OC(O)OR_1'$ or

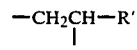

comprising contacting a lower alkyl carbonate or halogenated lower alkyl carbonate corresponding to the formula ROC(O)OR with a primary alkyl halide corresponding to the formula $R_1$-X or a vicinal alkyl dihalide having one primary halide functionality corresponding to the formula X-$R_2$-X at about 50° C. to 250° C. in the presence of an effective amount of an initiator selected from the group consisting of an alkali metal alkoxide, a salt of a strong base and a weak acid, a non-nucleophilic organic base, an alkali metal halide or a stable quaternary ammonium or phosphonium salt wherein:

R is independently each occurrence a lower alkyl or halogenated lower alkyl radical;

$R_1$ is different than R and is an alkyl radical of up to about 20 carbons optionally further substituted with alkenyl, aryl, halo, alkoxy or cyclic aliphatic or aromatic groups;

$R_1'$ is R or $R_1$;

$R_2$ is

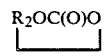

where R' is R or phenyl; and

X is halo.

2. The process of claim 1 wherein the initiator is present in an amount from about 0.01 to about 10 percent based on the weight of the reactants.

3. The process of claim 2 wherein the initiator is a tertiary amine of phosphine.

* * * * *